United States Patent
Yeh et al.

(10) Patent No.: US 6,308,576 B1
(45) Date of Patent: *Oct. 30, 2001

(54) METHOD FOR DETERMINING STRESS EFFECT ON A FILM DURING SCRUBBER CLEAN

(75) Inventors: Renn-Shyan Yeh, Taichun; Der-Fang Huang; Tzu-Yu Lin, both of Hsin-Chu; Chao-Hsin Chang, Tao-Yuan, all of (TW)

(73) Assignee: Taiwan Semiconductor Manufacturing Company, Ltd, Hsin Chu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 09/281,339

(22) Filed: Mar. 30, 1999

(51) Int. Cl.$^7$ .............................. G01B 11/16; G01B 21/32
(52) U.S. Cl. ................................................... 73/762
(58) Field of Search ............................... 73/762; 364/132; 134/6; 15/77; 438/515

(56) References Cited

U.S. PATENT DOCUMENTS

| | | | |
|---|---|---|---|
| 5,861,066 | * | 1/1999 | Moinpour et al. ...................... 134/6 |
| 5,862,560 | * | 1/1999 | Jensen et al. ............................. 15/77 |
| 5,864,393 | * | 7/1999 | Maris ..................................... 73/762 |
| 5,924,154 | * | 7/1999 | Maris ..................................... 73/762 |
| 5,975,736 | * | 11/1999 | Simmons et al. ..................... 364/132 |
| 6,153,497 | * | 11/2000 | Yeh et al. ............................. 438/515 |

* cited by examiner

Primary Examiner—Benjamin R. Fuller
Assistant Examiner—Detana Davis
(74) Attorney, Agent, or Firm—Tung & Associates

(57) ABSTRACT

A method for determining stress effects, or stress endurance of a film layer coated on a wafer during a scrubber clean process is disclosed. In the method, a wafer having a film layer coated on top is held in a stationary position while a high pressure water jet having a pressure larger than 60 kg/cm$^2$ is scanned across a top surface of the film layer and through a center of the wafer. The total number of stress defects is then counted in the scanning path on top of the film layer as an indication of the stress endurance of the specific coating layer. The invention also discloses a method for scrubber cleaning a wafer surface which is coated with a film layer without causing stress defects in the film by rotating a silicon wafer, which has a film layer coated on top at a suitable rotational speed, and then scanning a water jet across a top surface of the film layer without passing through a center of the wafer. The water pressure utilized for the water jet may be suitably between 50 kg/cm$^2$ and 75 kg/cm$^2$. It is preferred that the water jet does not pass any regions on the top surface of the film layer that is less than 2 mm from the center of the wafer.

18 Claims, 1 Drawing Sheet

METHOD FOR DETERMINING STRESS EFFECT ON A FILM DURING SCRUBBER CLEAN

FIELD OF THE INVENTION

The present invention generally relates to a method for scrubber clean a wafer with a surface coating and more particularly, relates to a method for determining a stress effect on a film coated on a wafer during a scrubber cleaning process.

BACKGROUND OF THE INVENTION

In the fabrication process for semiconductor devices, numerous fabrication steps, as many as several hundred, must be executed on a silicon wafer in order to complete the circuits on the device. Since the processing of silicon wafers requires extreme cleanliness in the processing environment and that no contaminating particles or films are allowed, the surface of the silicon wafer is frequently cleaned after each processing step. For instance, it is cleaned after the deposition of a surface coating layer such as oxide or after the formation of a circuit by a processing step such as etching. A frequently used method for cleaning the wafer surface is a wet scrubbing method.

In cleaning a wafer surface by a wet scrubbing method, a wafer is rotated at a high speed, i.e., at least 200 RPM and preferably 1,000 RPM, simultaneously with a jet of high pressure deionized water sprayed on top. The water jet is normally sprayed at a pressure of about 2,000~3,000 psi. The water movement on top of the wafer surface displaces any contaminating particles that is lodged on the wafer surface. One limitation of the water jet scrubbing is that the process only moves particles from side to side in openings, such as oxide windows, without removing the particle. Furthermore, as image size decreases, it becomes more difficult for water to reach the particles in openings because of increased surface tension.

It has also been noted that in a water jet scrubbing process conducted on a silicon wafer that is coated with an insulating material, i.e., an oxide layer as an inter-metal dielectric layer, some regions of the film is damaged at the wafer center by the cumulated stress from the water jet when the aperture size of the jet nozzle is too large or is distorted. The damaged film can be identified by a KLA scan, even though, a large number of wafers must be tested since the probability of such damage is only about 10~30%. This is shown in FIGS. 1 and 2.

FIG. 1 shows an illustration of a silicon wafer surface that is scanned in a conventional waterjet scrubbing method. Wafer 10 is normally positioned on a wafer platform (not shown) situated in a scrubbing apparatus and rotated at a predetermined rotational speed. A suitable rotational speed may be between 200 RPM and 2,000 RPM. The centrifugal force acting on the water flow on the wafer surface removes contaminating particles or films. The jet of deionized water which has a water pressure of approximately 50 kg/cm$^2$, is scanned on top of the wafer surface along trace 12 which normally goes through center 14 of the wafer 10. The wafer surface is scanned by the water jet at least once, and preferably several times.

A KLA scan on a wafer surface coated with an oxide film layer and scanned by a high pressure water jet is shown in FIG. 2. The black dots shown on the surface of the wafer indicate stress defects that have formed under the water jet pressure.

It has been noted that the stress defects only occur on certain types of surface coating layers and only for certain thicknesses of layer coated on a wafer surface. In the conventional water jet cleaning method, as shown in FIG. 1, it is difficult to identify which type of films will be damaged since the defects or damages are occurring only randomly at the wafer center. Furthermore, it is difficult to monitor whether the aperture in the jet nozzle is distorted or deformed.

It is therefore an object of the present invention to provide a method for determining stress defects on a film during a scrubber clean process that does not have the drawbacks or shortcomings of the conventional methods.

It is another object of the present invention to provide a method for determining stress defects on a coated film during a scrubber clean process which only requires one wafer sample to achieve a reliable determination.

It is a further object of the present invention to provide a method for determining stress defects on a coated film during a scrubber clean process that can be carried out on a single wafer sample scrubbed in a stationary position.

It is another further object of the present invention to provide a method for determining stress defects on a coated film during a scrubber clean process by utilizing a jet nozzle having a large aperture for enhancing the stress effect on the coated film.

It is still another object of the present invention to provide a method for determining the stress endurance of a film coated on a wafer during a scrubber clean process by a high pressure water jet of deionized water while holding the wafer stationary.

It is yet another object of the present invention to provide a method for determining stress effects on a film coated on a wafer during a water jet scrubber clean process in which the film is an inter-metal dielectric of PE oxide.

It is still another further object of the present invention to provide a method for scrubber clean a wafer surface coated with a film layer without causing stress defects in the film by positioning the wafer on a wafer platform and rotating the platform while scanning a water jet across a top surface of the film layer without passing through a center of the wafer.

It is yet another further object of the present invention to provide a method for scrubber clean a wafer surface coated with a film layer without causing stress defects in the film by scanning a water jet across a top surface of the film layer without passing through regions on the wafer that is less than 2 mm from the center of the wafer.

SUMMARY OF THE INVENTION

In accordance with the present invention, a method for determining stress defects on a film during a scrubber clean process and a method for scrubber clean a wafer surface coated with a film layer without causing stress defects in the film are disclosed.

In a preferred embodiment, a method for determining stress defects on a film during a scrubber clean process can be carried out by the operating steps of providing a semi-conducting wafer which has a film layer coated on top, positioning a wafer on a wafer holder in a scrubber chamber, scanning a water jet in a single pass across a top surface of the film on the wafer while passing through a center of the wafer and while holding the wafer in a stationary position, the water jet has a pressure of at least 50 kg/cm$^2$, and counting stress defects in the scanning path on top of the film layer.

The method for determining stress defects on a film during a scrubber clean process may further include the steps of providing a water jet nozzle which has an aperture of at least 0.2 mmn in diameter, and injecting a jet of water from the aperture impacting a top surface of the coated film. The semi-conducting wafer may be a silicon wafer. The film coated on top of the semi-conducting wafer may be an inter-metal dielectric (IMD) film. The film coated on top of the semi-conducting wafer is a plasma enhanced oxide film. The waterjet may be formed of deionized water. The film coated may be an insulating layer for forming a via hole therein. The water jet may have a water pressure of at least 50 kg/cm².

The present invention is further directed to a method for scrubber clean a wafer surface coated with a film layer without causing stress defects in the film by the operating steps of providing a silicon wafer which as a film layer coated on top, positioning the wafer on a wafer platform situated in a scrubber and rotating the platform and scanning a water jet in at least one pass across a top surface of the film layer without passing through a center of the wafer.

The method for scrubber clean a wafer surface may further include the step of scanning a water jet in at least one pass across a top surface of the film layer without passing through regions on the wafer that is less than 2 mm from a center of the wafer. The water jet may be formed of deionized water. The method may further include the step of depositing an inter-metal dielectric layer on top of the wafer, or the step of depositing an insulating material layer on top of the wafer, or the step of depositing an electrically conductive layer on top of the wafer. The water jet may have a water pressure of at least 50 kg/cm². The method may further include the step of providing a water jet nozzle which has an aperture of at least 0.05 mm in diameter, or preferably at least 0.1 mm in diameter. The method may still further include the step of rotating the wafer platform in the scrubber at a rotational speed of at least 200 RPM.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

The present invention discloses a method for determining stress effects, or stress defects on a coated film during the scrubber clean process of a semi-conducting wafer. The present invention is further directed to a method for scrubber clean a wafer surface coated with a film layer without causing stress defects in the film.

The present invention novel method for determining stress defects in a film layer can be used reliably to indicate the susceptibility of a specific film to stress defects during a scrubber clean process by water jet. When practicing the present invention novel method, the stress effects or the stress endurance of a specific film can be determined on a single wafer. This results in great savings in time and labor since conventionally, such determination requires a testing of at least 30~50 wafers. The present invention novel method for determining the stress defects or the stress endurance of a specific coated film, such as an insulating film of inter-metal dielectric material, can be carried out with the wafer in a stationary position by scanning the wafer surface through its center at a water pressure of at least 50 kg/cm². The water pressure can be easily achieved by using a water jet nozzle which has a nozzle aperture of at least 0.2 mm in diameter.

The present invention further provides a method for scrubber clean a wafer surface that is coated with a film layer without causing stress defects in the film by executing the scrubbing operation with a water jet scanning across a top surface of the wafer without passing through a center of the wafer while the wafer is rotated at a predetermined rotational speed. The method can be executed by scanning a water jet in at least one pass across a top surface of a wafer without passing through regions on the wafer that is less than 2 mm away from the center of the wafer. The water jet utilized is normally deionized water.

Figure 1:
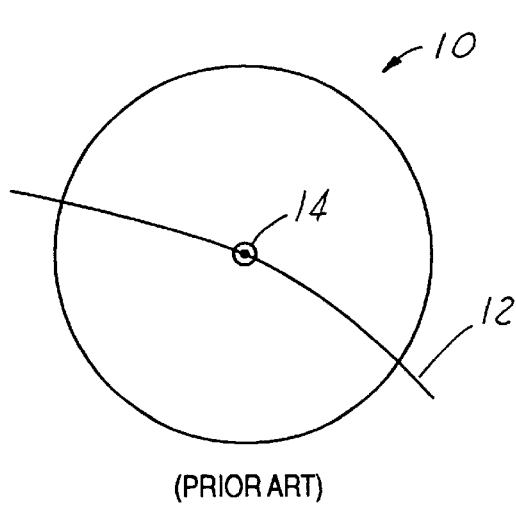
FIG. 1 is an illustration of a conventional method for cleaning a wafer positioned in a wet scrubber by a water jet traversing across a top surface and through a center of the wafer.
Figure 3:
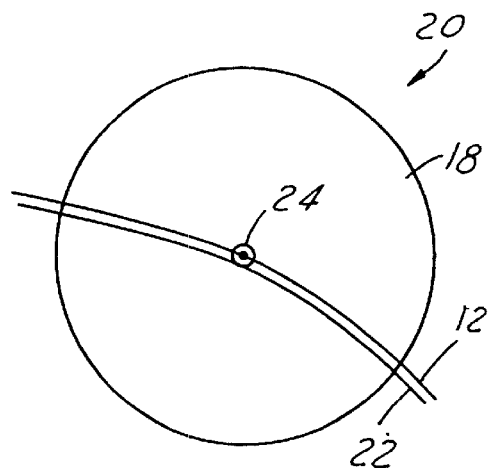
FIG. 3 is an illustration of the present invention method wherein a water jet is kept at least 2 mm from the center of the wafer.
Figure 2:
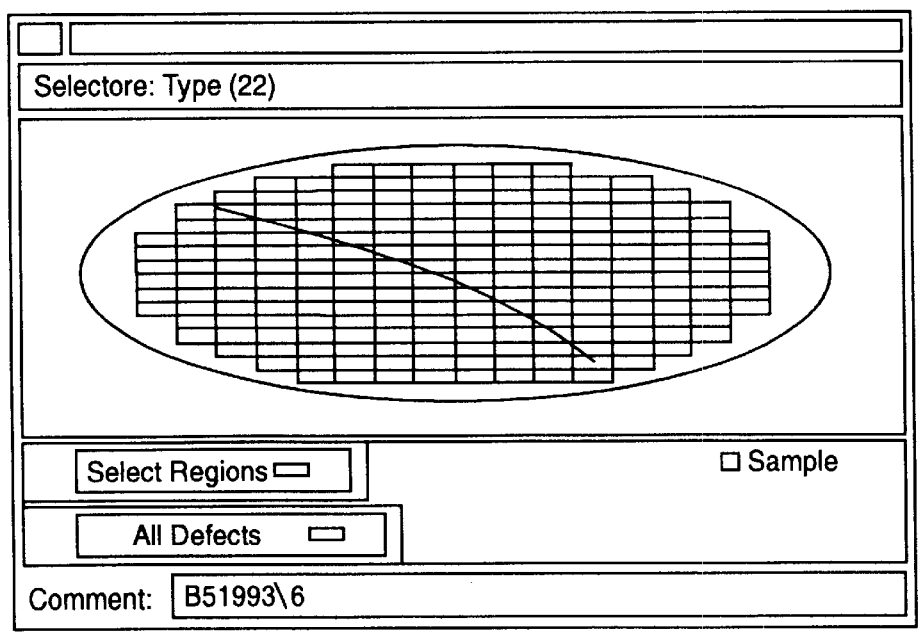
FIG. 2 is an illustration of a KLA scan obtained across the wafer surface that is scrubber cleaned by the conventional method of FIG. 1.

Referring now to FIG. 3 wherein a present invention novel method for scrubber clean a surface 18 of wafer 20 coated with a film layer without causing stress defects in the film is shown. A water jet 22 is scanned on the surface 18 in at least one pass across the film layer without passing through a center 24 of the wafer. It should be noted that, in FIG. 3, the conventional method which sweeps a waterjet 12 across the center 24 of the wafer is also shown for comparison. The novel method of the invention is carried out by scanning the water jet in at least one pass across the surface 18 of the wafer without passing through regions on the wafer that is less than 2 mm from the center 24 of the wafer 20.

The present invention novel method therefore provides a reliable means for determining stress effects or stress endurance in a coating layer on top of a wafer surface. The method is carried out by using a larger than normal aperture in the water jet nozzle, i.e., larger than 0.1 mm in diameter and preferably of a diameter of 0.2 mm. The larger diameter of the aperture in the water jet nozzle allows a higher water pressure to be impinged on the wafer surface, i.e., on top of the film coating layer, with a pressure higher than 50 kg/cm², preferably higher than 60 kg/cm² and more preferably higher than 70 kg/cm². By using the present invention novel method as a screening test, with the wafer in a stationary position, the stress endurance of the film can be easily predicted. For instance, whether a scrubber clean process would result in stress defects being generated on the film. It is therefore possible to determine whether a scrubber clean process should be conducted on certain wafers that have been coated with certain films.

Furthermore, the present invention novel method can be utilized to scrubber clean a wafer surface coated with a film layer without generating stress defects by scanning a water jet across the wafer surface, while the wafer is rotating, without passing through the wafer center. The stress defects, shown in the form of film cracks, have occurred in oxide films that are deposited as inter-metal dielectric layers on top of a silicon wafer. It has been found that cumulating stress and energy from the scrubber jet at the wafer center is the main cause for stress defects such as via film cracks. By increasing the nozzle aperture dimension, the cumulated energy per unit time is proportionally increased. This is shown in the following equations:

$$W = F \times d = P \times A \times d = E = \tfrac{1}{2} m_1 v_1^2 = \tfrac{1}{2} m_2 v_2^2$$

since $m_1=m_2=A\times d\times 1=m$ (The density of water is 1) and $v_1=v_2=v$

The velocity of water is constant when P is constant.

$$J = \frac{dm}{dt} = a \cdot v \cdot 1\alpha\ d \text{ (The discharge rate is proportional to the area of nozzle.)}$$

$$\omega = \frac{dW}{dt} = \frac{1}{2}v^2 \cdot \frac{dm}{dt} = \frac{1}{2}dv^3 \alpha\ d$$

$$\text{If } a_1 = 4a_2 \text{ then } w_1 = 4w_2$$

Wherein

W: Work;

E: Kinetic Energy;

P: Air pressure on the piston;

A: Area of piston;

a: Aperture size of nozzle;

d: Displacement of piston;

j: Discharge rate

ω: Power=dW/dt

It is therefore clearly shown that when the aperture size of the water nozzle is increased, the cumulating power acting on the wafer surface is proportionally increased.

The present invention novel method for determining stress effects or stress endurance in a film layer coated on a wafer during a water jet scrubber clean process and a method for scrubber clean a wafer surface coated with a film layer without causing stress defects have therefore been amply demonstrated in the above descriptions and in the appended drawing of FIG. 3.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

What is claimed is:

1. A method for determining stress defects on a film during a scrubber cleaning process comprising the steps of:

providing a semi-conducting wafer having a film coated on top, positioning said wafer on a wafer holder in a scrubber chamber and holding said wafer holder in a stationary position, scanning a water jet in a single scanning path across a top surface of said film on top of said wafer while passing through a center of said wafer, said water jet having a water pressure of at least 50 kg/cm², and counting stress defects in said single scanning path on top of said film layer.

2. A method for determining stress defects in a film during a scrubber clean process according to claim 1 further comprising the steps of:

providing a wafer jet nozzle having an aperture of at least 0.2 mm in diameter, and injecting a jet of water from said aperture impacting a top surface of said coated film.

3. A method for determining stress defects in a film during a scrubber clean process according to claim 1, wherein said semi-conducting wafer is a silicon wafer.

4. A method for determining stress defects in a film during a scrubber clean process according to claim 1, wherein said film coated on top of said semi-conducting wafer is an inter-metal dielectric film.

5. A method for determining stress defects in a film during a scrubber clean process according to claim 1, wherein said film coated on top of said semi-conducting wafer is a plasma enhanced oxide film.

6. A method for determining stress defects in a film during a scrubber clean process according to claim 1, wherein said water jet is formed of deionized water.

7. A method for determining stress defects in a film during a scrubber clean process according to claim 1, wherein said film coated is an insulating layer.

8. A method for determining stress defects in a film during a scrubber clean process according to claim 1, wherein said water jet has a water pressure of at least 70 kg/cm².

9. A method for scrubber cleaning a wafer surface coated with a film layer without causing stress defects in the film comprising the steps of:

providing a silicon wafer having a film layer coated on top, positioning the wafer on a wafer platform and rotating the platform in a scrubber, and scanning a water jet in at least one scanning path across a top surface of said film layer without passing through a center of the wafer.

10. A method for scrubber cleaning a wafer surface coated with a film layer without causing stress defects in the film according to claim 9 further comprising the step of scanning a water jet in at least one pass across a top surface of said film layer without passing through regions on said wafer that are less than 2 mm from said center of the wafer.

11. A method for scrubber cleaning a wafer surface coated with a film layer without causing stress defects in the film according to claim 9, wherein said water jet is formed of deionized water.

12. A method for scrubber cleaning a wafer surface coated with a film layer without causing stress defects in the film according to claim 9 further comprising the step of depositing a inter-metal dielectric layer on top of said wafer.

13. A method for scrubber cleaning a wafer surface coated with a film layer without causing stress defects in the film according to claim 9 further comprising the step of depositing an insulating material layer on top of said wafer.

14. A method for scrubber cleaning a wafer surface coated with a film layer without causing stress defects in the film according to claim 9 further comprising the step of depositing an electrically conductive layer on top of said wafer.

15. A method for scrubber cleaning a wafer surface coated with a film layer without causing stress defects in the film according to claim 9, wherein said water jet has a water pressure of at least 50 kg/cm².

16. A method for scrubber cleaning a wafer surface coated with a film layer without causing stress defects in the film according to claim 9 further comprising the step of providing a water jet nozzle having an aperture of at least 0.05 mm in diameter.

17. A method for scrubber cleaning a wafer surface coated with a film layer without causing stress defects in the film according to claim 9 further comprising the step of providing a water jet nozzle having an aperture of at least 0.1 mm in diameter.

18. A method for scrubber cleaning a wafer surface coated with a film layer without causing stress defects in the film according to claim 9 further comprising the step of rotating said wafer platform in said scrubber at a rotational speed of at least 200 RPM.

* * * * *